(12) United States Patent
Zhang et al.

(10) Patent No.: US 8,697,291 B2
(45) Date of Patent: Apr. 15, 2014

(54) NON-AQUEOUS ELECTROLYTE FOR LITHIUM-ION BATTERY

(75) Inventors: Lu Zhang, Woodridge, IL (US); Zhengcheng Zhang, Naperville, IL (US); Khalil Amine, Oakbrook, IL (US)

(73) Assignee: UChicago Argonne, LLC, Chicago, IL (US)

( * ) Notice: Subject to any disclaimer, the term of this patent is extended or adjusted under 35 U.S.C. 154(b) by 584 days.

(21) Appl. No.: 12/899,722

(22) Filed: Oct. 7, 2010

(65) Prior Publication Data

US 2012/0088160 A1    Apr. 12, 2012

(51) Int. Cl.
*H01M 10/0562* (2010.01)
*H01M 6/18* (2006.01)

(52) U.S. Cl.
USPC ............................. 429/314; 429/321; 429/324

(58) Field of Classification Search
USPC .......................................... 429/314, 321, 324
See application file for complete search history.

(56) References Cited

U.S. PATENT DOCUMENTS

| | | | |
|---|---|---|---|
| 5,626,981 A | 5/1997 | Simon et al. | |
| 2004/0157126 A1 | 8/2004 | Belharouak et al. | |
| 2005/0019670 A1 | 1/2005 | Amine et al. | |
| 2006/0276644 A1 | 12/2006 | Childress et al. | |

FOREIGN PATENT DOCUMENTS

| CN | 101643452 | 2/2010 | | |
|---|---|---|---|---|
| EP | 0 490 048 | 8/1997 | | |
| JP | 62-290072 | 12/1987 | | |
| JP | 04-095362 | 3/1992 | | |
| JP | 2962782 | 10/1999 | | |
| JP | 2001-155772 | * 6/2001 | ............ | H01M 10/40 |
| JP | 2002-358999 | * 12/2002 | ............ | H01M 10/40 |
| WO | WO-98/15024 | 4/1998 | | |
| WO | WO-00/79632 | 12/2000 | | |

OTHER PUBLICATIONS

U.S. Appl. No. 60/636,636, filed Dec. 16, 2004, Argonne National Laboratory.
U.S. Appl. No. 60/647,361, filed Jan. 1, 2005, Argonne National Laboratory.
Chung, G. et al., "Origin of Graphite Exfoliation. An Investigation of the Important Role of Solvent Cointercalation", Journal of Electrochemical Society, 2000, vol. 147(12), pp. 4391-4398.
Duong, H. A. et al., "N-Heterocyclic carbenes as highly efficient catalysts for the cyclotrimerization of isocyanates," Organic Letters, 2000, vol. 6(25), pp. 4679-4681.
Fleming, I., "(E)-1-Trimethylsilyl-1,3-butadiene," e-EROS (Encyclopedia of Reagents for Organic Synthesis online), 2001. (Abstract Only).
Graham, J. C. et al., "Bis(ethyl-3-oxobutanolato-O1,O3)-bis(2-propanolato)titanium (Tyzor DC) as a reactant and catalyst in the trimerization of 2-isocyanatoethyl methacrylate (IEM)," Catalysis Letters, Sep. 1989, vol. 3(5-6), pp. 413-420.

(Continued)

*Primary Examiner* — Helen O Conley
(74) *Attorney, Agent, or Firm* — Foley & Lardner LLP

(57) ABSTRACT

The present technology relates to stabilizing additives and electrolytes containing the same for use in electrochemical devices such as lithium ion batteries and capacitors. The stabilizing additives include triazinane triones and bicyclic compounds comprising succinic anhydride, such as compounds of Formulas I and II described herein.

10 Claims, 8 Drawing Sheets

(56) References Cited

OTHER PUBLICATIONS

Gu, X. et al., "Synthesis of the constrained glutamate analogs (2S,1'R,2'R)- and (2S,1'S,2'S)-2-(2'-carboxycyclobutyl) glycines L-CBG-II and L-CBG-I by enzymatic transamination," Tetrahedron Letters, 2005, vol. 47(2), pp. 193-196.

Havet, J. et al., "Synthesis and N-Methylation of Tetrabutylammonium Isocyanurate," Tetrahedron Letters, 2003, vol. 44(23), pp. 4399-4402.

Padwa, A. et al., "Reactivity patterns in the rhodium carbenoid induced tandem cyclization-cycloaddition reaction," Journal of Organic Chemistry, 1989, vol. 54(4), pp. 817-824.

Simpkins, L. et al., "Potent Non-Nitrile Dipeptidic Dipeptidyl Peptidase IV Inhibitors," Bioorganic & Medicinal Chemistry Letters, Dec. 2007, vol. 17(23), pp. 6476-6480.

Doering, W. et al, "Fate of the Intermediate Diradicals in the Caldera: Stereochemistry of Thermal Stereomutations, (2+2) Cycloreversions, and (2+4) Ring-Enlargements of cis- and trans- 1-Cyano-2-(E and Z)-propenyl-cis-3,4-dideuteriocyclobutanes," Journal of the American Chemical Society, 2002, vol. 124(39), pp. 11642-11652.

Xu, K. et al., "Lithium Bis(oxalato)borate Stabilizes Graphite Anode in Propylene Carbonate", Electrochemical and Solid-State Letters, 2002, vol. 5(11), pp. A259-A262.

Zhang et al., "Non-aqueous electrolyte for lithium-ion batteries", Argonne National Laboratory, May 17, 2010, 12 pps.

* cited by examiner

NON-AQUEOUS ELECTROLYTE FOR LITHIUM-ION BATTERY

GOVERNMENT INTERESTS

This invention was made with Government support under Contract No. W-31-109-ENG-38 awarded by the Department of Energy. The Government has certain rights in this invention.

FIELD

The present technology relates in general to the field of lithium rechargeable batteries, and more particularly relates to the use of reduction oxidation (e.g redox) shuttles in electrochemical cells and batteries.

BACKGROUND

The tremendous advances in science and engineering related to lithium-ion batteries have made such batteries the most popular power source for portable electronic devices. Furthermore, lithium-ion batteries have been proposed for new applications in powering electric and hybrid electric vehicles.

Electrolytes are a ubiquitous and indispensable component of lithium-ion batteries. Because the electrolyte is sandwiched between positive and negative electrodes, the electrolyte is in close interaction with both electrodes. The interfaces between the electrolyte and the two electrodes often dictate the performance of the cells. In particular, the interface between the anode and the is a crucial factor affecting cell performance. The interface is a thin passivation layer, also called SEI (solid electrolyte interface), which is formed during the first charging process and prevents further reaction of the electrolytes on the anode surface. For fuel cells utilizing carbon anodes, the formation process is potential dependant and stepwise, and is determined by the reactive components of the electrolytes that participate in the formation reactions. Therefore, the SEI layer can be tuned to afford better cell performance through the use of various additives.

State-of-the-art electrolytes for lithium-ion batteries include lithium hexafluorophosphate ($LiPF_6$) as solute and mixtures of cyclic carbonates and linear carbonates as solvents. Ethylene carbonate (EC) is a cyclic carbonate typically used in electrolytes for the formation of SEI at the surface of the negative electrode. However, in many cases the SEI protection from conventional electrolytes with simple formulations such as $LiPF_6$ in admixtures with EC and linear carbonates is insufficient in lithium ion batteries where the negative electrode materials are carbonaceous materials. For instance, when cycling under elevated temperature, the capacities of lithium-ion batteries can fade very quickly. Another issue occurs when using carbonaceous anodes. Batteries that employ either inexpensive natural graphite (a kind of graphite carbon) or hard carbon (a kind of amorphous non-graphite carbon), exhibit a larger initial discharge capacity loss and quickly lose capacity in subsequent cycles.

On the other hand, EC has a high melting point, at about 36-38° C., which limits the performance of lithium ion batteries containing EC-based electrolytes in low temperature applications. Thus propylene carbonate (PC) which has a structure similar to that of EC has been considered to fully or partially replace EC because PC remains in the liquid state over a wide temperature window from −55° C. to 240° C. However, $LiPF_6$—PC based electrolytes are not compatible with graphite electrodes in lithium ion batteries due to the exfoliation of graphite structure by PC intercalation.

SUMMARY

The present technology is generally related to substantially non-aqueous electrolytes including one or more stabilizing additives, the additives themselves and electrochemical devices employing such electrolytes and exhibiting a long cycle life and a high capacity retention for lithium metal. Specifically, the present technology provides a non-aqueous electrolytic solution having one or more cyclic organic compounds, such as triazinane triones and/or bicyclic compounds including a succinic anhydride group that improve SEI film formation on disordered graphite electrodes or other carbonaceous electrodes. Such stabilizing additives include, among others, 1,3,5-triallyl-1,3,5-triazine-2,4,6(1H,3H,5H)-trione (TTT) and 3-oxabicyclo[3.1.0]hexane-2,4-dione (OHD), and their derivatives. The additives in non-aqueous electrolytic solutions may be used in rechargeable batteries, reducing or preventing PC intercalation into the carbon electrodes and providing long life and high capacity retention at elevated temperature.

DETAILED DESCRIPTION

Figure 1:
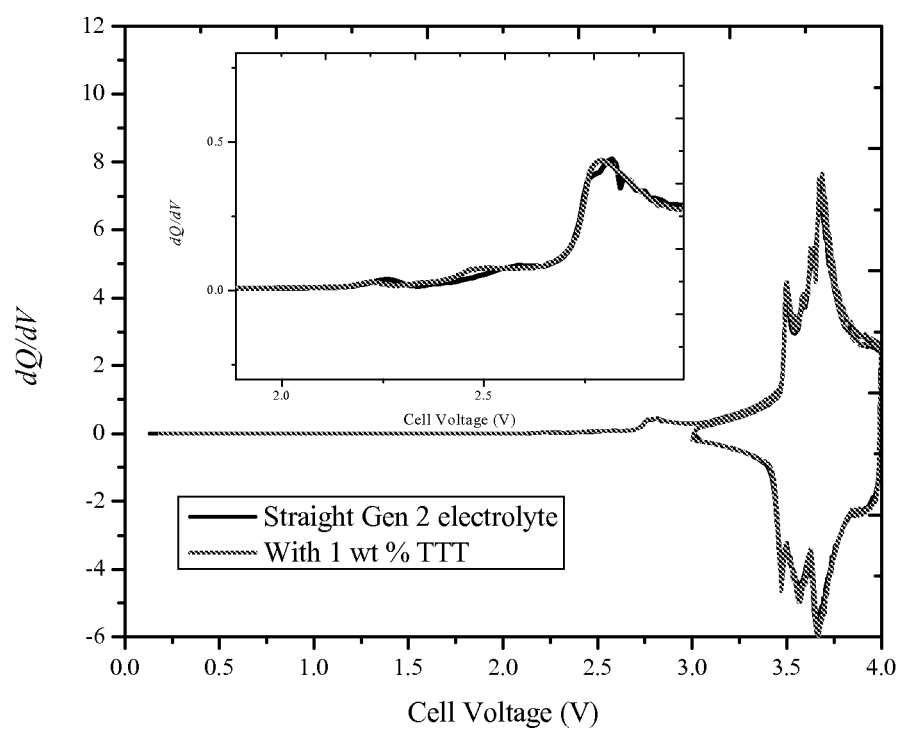
FIG. 1: Differential capacity profiles of the mesocarbon microbead (MCMB)/$Li_{1.1}[Ni_{1/3}Co_{1/3}Mn_{1/3}]_{0.9}O_2$ 2032 lithium-ion coin cells during the initial formation process in EC/ethyl methyl carbonate (EMC), 3:7 by weight (Gen 2 electrolyte), with or without 1 wt % additives. The cells were cycled at 55° C. between 3~4 V with a constant current of 1 C (~2.0 mA).

The present technology relates to electrolytes containing stabilizing additives that improve the SEI in electrochemical devices such as lithium ion batteries. More specifically, the stabilizing additives of the present technology can form a stable passivation film between electrodes and electrolyte, which improves the cycle life of, e.g., lithium-ion batteries.

In accordance with one aspect of the present technology, there are provided electrolytes that include an alkali metal salt; a polar aprotic solvent; and one or more stabilizing additives. At least one of the stabilizing additives is selected from a triazinane trione and/or a bicyclic compound comprising succinic anhydride. The electrolytes are substantially non-aqueous, i.e., the electrolytes contain either no water or almost no water (e.g., <100 ppm water). In some embodiments, at least one of the stabilizing additives is a 1,3,5-triazinane-2,4,6-trione. In certain embodiments, the stabilizing additives include one or more alkenyl groups.

In some embodiments of the present electrolytes, at least one of the stabilizing additives is selected from the group consisting of a compound of formula I and a compound of formula II:

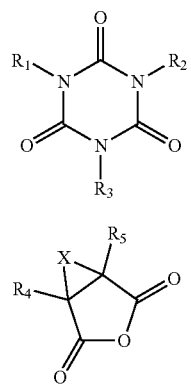

wherein:
$R^1$, $R^2$, $R^3$, $R^4$ and $R^5$ are independently H, F, Cl, Br, CN, $NO_2$, a substituted or unsubstituted alkyl, alkoxyalkyl, alkenyl, alkynyl group, organophosphate, an ester group, a substituted or unsubstituted siloxyalkyl group, a substituted or unsubstituted silylalkyl group, a substituted or unsubstituted epoxy or epoxyalkyl group, a substituted or unsubstituted carbonate group, a substituted or unsubstituted ethylene carbonate group, a substituted or unsubstituted vinyl carbonate group, or a substituted or unsubstituted vinyl ethylene carbonate group;

X is selected from a group of formula IIIA, IIIB, IIIC, IIID, or IIIE

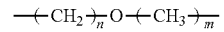

IIIA

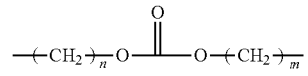

IIIB

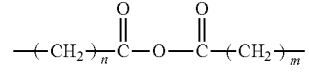

IIIC

IIID

IIIE $R^6$ and $R^7$ are independently H, F, Cl, Br, a substituted or unsubstituted alkyl, alkenyl, or alkynyl group;

n is an integer from 1 to 6 for formula IIIA and from 0 to 4 for formulas IIIB-IIIE; and m is an integer from 0 to 4 such that the sum of n and m is not greater than 4.

In some embodiments of the present technology, $R^1$, $R^2$, $R^3$, $R^4$ and $R^5$ are independently selected from H, F, Cl, Br, I, an unsubstituted alkyl or alkenyl group, a haloalkyl group, an epoxyalkyl group, or an alkyl, alkenyl or alkoxyalkyl group substituted with a substituent selected from the group consisting of ethylene carbonate, vinyl ethylene carbonate, vinyl carbonate, and an ester. In some embodiments, the ester is acrylate. In others, $R^1$, $R^2$, $R^3$, $R^4$ and $R^5$ are independently selected from H, F, Cl, Br, I, an unsubstituted $C_1$-$C_4$ alkyl group, an unsubstituted $C_2$-$C_6$ alkenyl group, an unsubstituted $C_2$-$C_6$ alkynyl group, a $C_1$-$C_4$ alkyl group substituted with a $C_2$-$C_6$ ester group, a $C_4$-$C_8$ silylalkyl group, a $C_4$-$C_8$ siloxylalkyl group, a $C_2$-$C_4$ alkoxyalkyl group substituted with an ethylene carbonate group, or a $C_2$-$C_{10}$ epoxy or epoxyalkyl group. In certain embodiments, $R^1$, $R^2$, $R^3$, $R^4$ and $R^5$ are independently selected from the group consisting of methyl, ethyl, n-propyl, iso-propyl, n-butyl, sec-butyl, tert-butyl, vinyl, 2-propenyl, 3-butenyl, acetylenyl, 2-propynyl, and 3-butynyl. $R^1$, $R^2$, and $R^3$ may be the same or different. $R^4$ and $R^5$ may also be the same or different. For example, $R^4$ and $R^5$ may both be H, or $R^1$, $R^2$, and $R^3$ may each be an allyl group.

The compound of formula II is a bicyclic structure in which the ring including the variable X may have a variety of sizes and chemical structures. For example, in addition to the definitions provided above, when X has the structure of formula IIIA and n is an integer from 1 to 4, the compound of formula II includes cyclopropyl, cyclobutyl, cyclopentyl and cyclohexyl groups. When X has the formula IIIB, IIIC, IIID, or IIIE and n and m are independently 0 or 1, the compound of formula II may include 4-6 member cycloalkenes (IIIB), 3-5 member cyclic ethers (IIIC), 5-7 member cyclic carbonates (IIID), and 5-7 member cyclic anhydrides (IIIE).

In some embodiments of the present electrolytes, at least one stabilizing additive is selected from the group consisting of

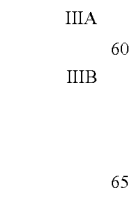

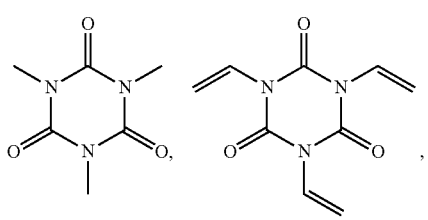

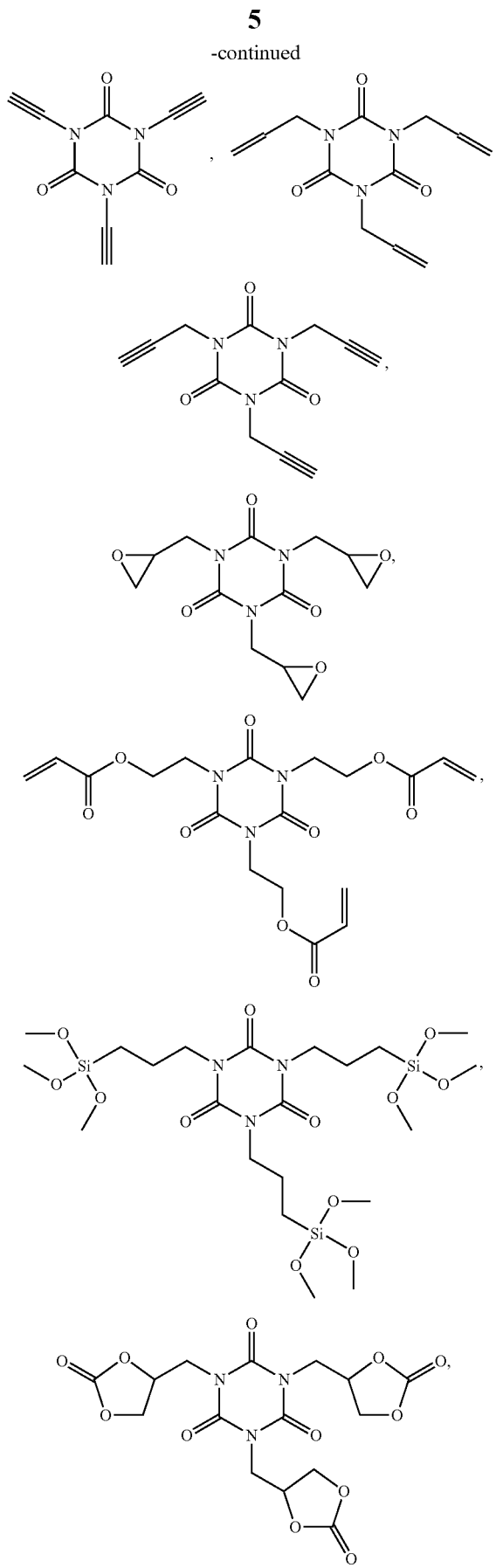
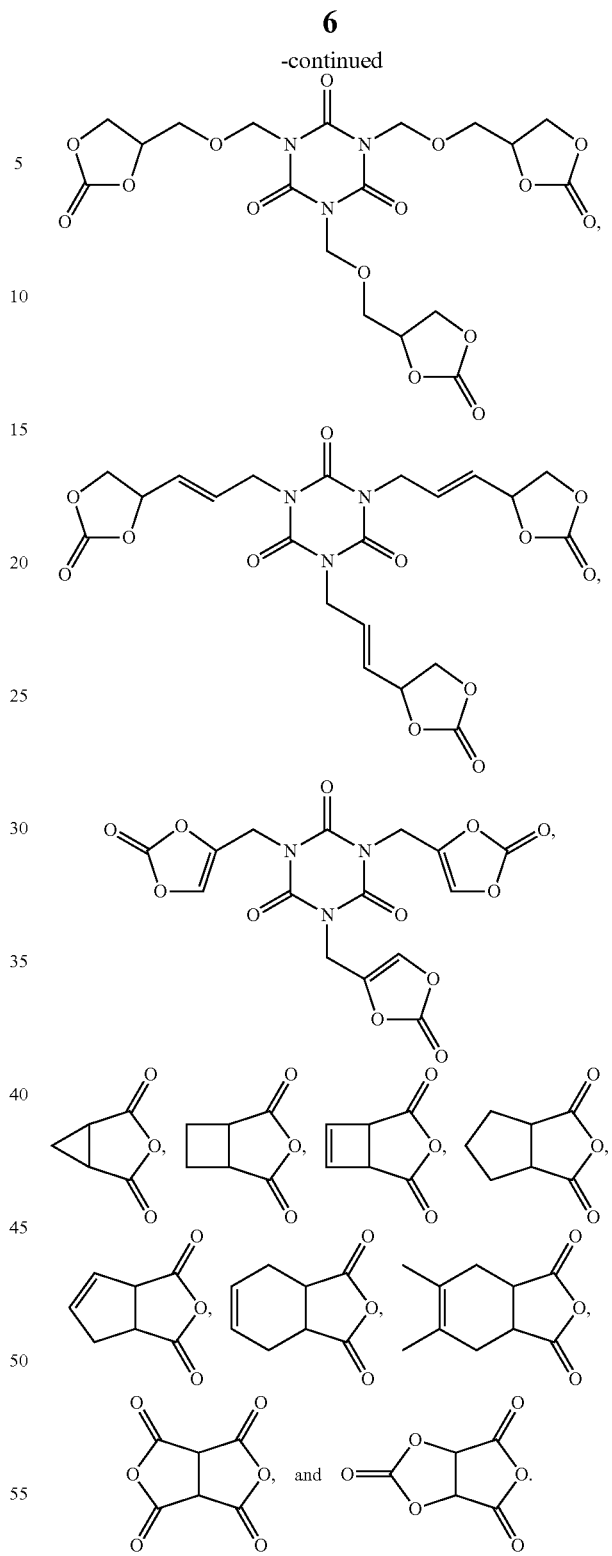

The stabilizing additives may be present in the electrolytes of the present technology at a wide variety of concentrations, such as, e.g., from 0.0005 wt % to 15 wt %, 30 wt % or 50 wt % of the electrolyte. In some embodiments the concentration of stabilizing additive ranges from 0.001 wt % to 2 wt %, to 5 wt %, to 10 wt %, to 15 wt %, to 20 wt %, to 25 wt %, to 30 wt %, to 40 wt % or to 50 wt %. In other embodiments the stabilizing additive ranges from 0.01 wt % to 2 wt %, to 5 wt %, 10 wt %, to 15 wt %, to 20 wt %, to 25 wt %, to 30 wt %, to 40 wt % or to 50 wt %, or from 0.1 wt % to 2 wt %, to 5 wt %, to 10 wt %, to 15 wt %, to 20 wt %, to 25 wt %, to 30 wt %, to 40 wt % or to 50 wt %. In still other embodiments, the concentration of stabilizing additive ranges from 0.01 wt % to 0.1 wt %, to 0.2 wt %, to 0.5 wt %, to 1 wt %, to 2 wt %, or to 5 wt %.

Electrolytes of the present technology may include additional stabilizing additives in addition to at least one compound of Formula I or Formula II. (See e.g., co-pending U.S. application Ser. No. 10/857,365; and provisional application Nos. 60/636,636 and 60/647,361.) Thus, electrolytes of the present technology can include additional stabilizing additives that can be reduced or polymerized on the surface of a negative electrode to form a passivation film on the surface of negative electrode. Likewise, inventive electrolytes can include an electrode stabilizing additive that can be oxidized or polymerized on the surface of the positive electrode to form a passivation film on the surface of the positive electrode. In some embodiments electrolytes of the present technology further include mixtures of the two types of electrode stabilizing additives. The additional additives are typically present at a concentration of from 0.001 wt % to 8 wt %.

Representative additional stabilizing additives include pyridazine, vinyl pyridazine, quinoline, vinyl quinoline, pyridine, vinyl pyridine, indole, vinyl indole, triethanolamine, 1,3-dimethyl butadiene, butadiene, vinyl ethylene carbonate, vinyl carbonate, imidazole, vinyl imidazole, piperidine, vinyl piperidine, pyrimidine, vinyl pyrimidine, pyrazine, vinyl pyrazine, isoquinoline, vinyl isoquinoline, quinoxaline, vinyl quinoxaline, biphenyl, 1,2-diphenyl ether, 1,2-diphenylethane, o-terphenyl, N-methylpyrrole, naphthalene, 3,9-divinyl-2,4,8,10-tetraoxaspiro[5.5]undecane, 3,9-divinyl-2,4,8-trioxaspiro[5.5]undecane, 3,9-divinyl-2,4-dioxaspiro[5.5]undecane, 3,9-diethylidene-2,4,8,10-tetraoxaspiro[5.5]undecane, 3,9-diethylidene-2,4,8-trioxaspiro[5.5]undecane, 3,9-diethylidene-2,4-dioxaspiro[5.5]undecane, 3,9-dimethylene-2,4,8,10-tetraoxaspiro[5.5]undecane, 3,9-divinyl-1,5,7,11-tetraoxaspiro[5.5]undecane, 3,9-dimethylene-1,5,7,11-tetraoxaspiro[5.5]undecane, 3,9-diethylidene-1,5,7,11-tetraoxaspiro[5.5]undecane, or a mixture of any two or more thereof.

Other stabilizing additives suitable for use in the electrolytes of the present technology include substituted or unsubstituted spirocyclic hydrocarbons containing at least one oxygen atom and at least one alkenyl or alkynyl group. For example, such stabilizing additives include those having Formula V:

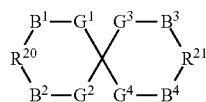

V wherein
$B^1$, $B^2$, $B^3$, and $B^4$ are independently O or $CR^{22}R^{23}$; provided that $B^1$ is not O when $G^1$ is O, $B^2$ is not O when $G^2$ is O, $B^3$ is not O when $G^3$ is O, and $B^4$ is not O when $G^4$ is O;

$G^1$, $G^2$, $G^3$, and $G^4$ are independently O or $CR^{22}R^{23}$; provided that $G^1$ is not O when $B^1$ is O, $G^2$ is not O when $B^2$ is O, $G^3$ is not O when $B^3$ is O, and $G^4$ is not O when $B^4$ is O;

$R^{20}$ and $R^{21}$ are independently a substituted or unsubstituted divalent alkenyl or alkynyl group;

$R^{22}$ and $R^{23}$ at each occurrence are independently H, F, Cl, a substituted or an unsubstituted alkyl, alkenyl, or alkynyl group.

Representative examples of Formula V include but are not limited to 3,9-divinyl-2,4,8,10-tetraoxaspiro[5.5]undecane, 3,9-divinyl-2,4,8-trioxaspiro[5.5]undecane, 3,9-divinyl-2,4-dioxaspiro[5.5]undecane, 3,9-diethylidene-2,4,8,10-tetraoxaspiro[5.5]undecane, 3,9-diethylidene-2,4,8-trioxaspiro[5.5]undecane, 3,9-diethylidene-2,4-dioxaspiro[5.5]undecane, 3,9-dimethylene-2,4,8,10-tetraoxaspiro[5.5]undecane, 3,9-divinyl-1,5,7,11-tetraoxaspiro[5.5]undecane, 3,9-dimethylene-1,5,7,11-tetraoxaspiro[5.5]undecane, 3,9-diethylidene-1,5,7,11-tetraoxaspiro[5.5]undecane, or a mixture of any two or more thereof.

The present electrolytes include an alkali metal salt dissolved in a polar aprotic solvent. The alkali metal salt can be present at a concentration of from about 0.5 to about 2 molar and may be a lithium salt. For example, the alkali metal salt may be $Li[(C_2O_4)_2B]$, $Li(C_2O_4)BF_2$, $LiClO_4$, $LiBF_4$, $LiAsF_6$, $LiPF_6$, $LiCF_3SO_3$, $Li(CF_3SO_2)_2N$, $Li(CF_3SO_2)_3C$, $LiN(SO_2C_2F_5)_2$, lithium alkyl fluorophosphates, or a mixture of any two or more thereof. Lithium(chelato)borates such as $Li[(C_2O_4)_2B]$ and $Li(C_2O_4)BF_2$ can also be used as the alkali metal salt, or as an additional stabilizing additive. Thus, in some embodiments, the alkali metal salt is other than a lithium(chelato)borate and the electrolyte further includes 0.0005 wt % to 15 wt % $Li[(C_2O_4)_2B]$ or $Li(C_2O_4)BF_2$.

A wide variety of polar aprotic solvents may be used in the present electrolytes including, but not limited to ethylene carbonate, propylene carbonate, dimethyl carbonate; ethyl methyl carbonate; diethyl carbonate; methyl propyl carbonate; ethyl propyl carbonate; dipropyl carbonate; bis(trifluoroethyl) carbonate; bis(pentafluoropropyl) carbonate; trifluoroethyl methyl carbonate; pentafluoroethyl methyl carbonate; heptafluoropropyl methyl carbonate; perfluorobutyl methyl carbonate; trifluoroethyl ethyl carbonate; pentafluoroethyl ethyl carbonate; heptafluoropropyl ethyl carbonate; perfluorobutyl ethyl carbonate; fluorinated oligomers; dimethoxyethane; triglyme; dimethylvinylene carbonate; tetraethyleneglycol; dimethyl ether; polyethylene glycols; sulfones; butyrolactone and mixtures of any two or more thereof. Protic solvents such as water and alcohols can not be used with the present technology.

In another aspect, the present technology provides methods of preparing the electrolytes described herein. The methods include combining an alkali metal salt and one or more stabilizing additives in a polar aprotic solvent substantially free of water; wherein at least one of the stabilizing additives is selected from the group consisting of a triazinane trione and a bicyclic compound comprising succinic anhydride. In some embodiments of the methods, the electrode stabilizing additive can be a compound of Formula I. In another embodiment, the electrode stabilizing additive may be a compound of Formula II. The present methods can employ any of the alkali metal salts or polar aprotic solvents described herein.

In another aspect, the present technology provides electrochemical devices incorporating the present electrolytes. The electrochemical device may be an electrochemical cell and include a cathode; an anode; and an electrolyte as described herein. The electrochemical device may be a lithium secondary battery. In some such batteries the cathode can be a lithium metal oxide cathode; the anode can be a carbon or lithium metal anode; and the anode and cathode are separated from each other by a porous separator.

Thus, for example, the cathode in such a device may include spinel, olivine, carbon-coated olivine (see Published U.S. Patent Application No. 2004/0157126), $LiFePO_4$, $LiCoO_2$, $LiNiO_2$, $LiNi_{1-x}Co_yMet_zO_2$, $LiMn_{0.5}Ni_{0.5}O_2$, $LiMn_{0.3}Co_{0.3}Ni_{0.3}O_2$, $LiMn_2O_4$, $LiFeO_2$, $LiMet_{0.5}Mn_{1.5}O_4$, $Li_{1+x'}Ni_\alpha Mn_\beta Co_\gamma Met'_\delta O_{2-z'}F_{z'}$, $A_{n'}B_2(YO_4)_3$ (Nasicon), vanadium oxide, or mixtures of any two or more thereof, wherein Met is Al, Mg, Ti, B, Ga, Si, Mn, or Co; Met' is Mg, Zn, Al, Ga, B, Zr, or Ti; A is Li, Ag, Cu, Na, Mn, Fe, Co, Ni, Cu, or Zn; B is Ti, V, Cr, Fe, or Zr; Y is P, S, Si, W, or Mo; $0 \le x \le 0.3$, $0 \le y \le 0.5$, $0 \le z \le 0.5$; $0 \le x' \le 0.4$, $0 \le \alpha \le 1$, $0 \le \beta \le 1$, $0 \le \gamma \le 1$, $0 \le \delta \le 0.4$, and $0 \le z' \le 0.4$; and $0 \le n' \le 3$. In some embodiments, the cathode can be a spinel manganese oxide with the formula of $Li_{1+x}Mn_{2-z}Met_yO_{4-s}Y_t$, wherein Met is Al, Mg, Ti, B, Ga, Si, Ni, or Co; Y is S or F; and wherein $0 \le x \le 0.3$, $0 \le y \le 0.5$, $0 \le z \le 0.5$, $0 \le s \le 0.5$ and $0 \le t \le 0.5$. Alternatively, the cathode can comprise olivine with a formula of $LiFe_{1-z}Met''_yPO_{4-s}Y_t$, wherein Met'' is Al, Mg, Ti, B, Ga, Si, Ni, Mn or Co; Y is S or F; and wherein $0 \le x \le 0.3$; $0 \le y \le 0.5$, $0 \le z \le 0.5$, $0 \le s \le 0.5$ and $0 \le t \le 0.5$.

In electrochemical devices of the present technology, the anode may comprise graphite, amorphous carbon, $Li_4Ti_5O_{12}$, tin alloys, silicon alloys, intermetallic compounds, lithium metal, or mixtures of any two or more thereof. Suitable graphitic materials including natural graphite, artificial graphite, graphitized meso-carbon microbeads, and graphite fibers, as well as any amorphous carbon materials.

Cathodes of the present technology may be further stabilized by surface coating the particles of the spinel or olivine with a material that can neutralize acid or otherwise lessen or prevent leaching of the manganese or iron ions. Hence the cathodes can also comprise a surface coating of a metal oxide on the spinel or olivine particles such as $ZrO_2$, $TiO_2$, $ZnO_2$, $WO_3$, $Al_2O_3$, $MgO$, $SiO_2$, $SnO_2$ $AlPO_4$, $Al(OH)_3$, a mixture of any two or more thereof, or any other suitable metal oxide. The coating can also be applied to a carbon coated olivine. Where carbon coated olivine is used, the metal oxide coating can be applied to the carbon coated olivine or can be applied to the olivine first followed by carbon coating of the metal oxide film. Methods for coating spinel cathodes with metal oxides are disclosed below and may be adapted for use with olivine cathodes.

The metal oxide coating on spinel can be applied using a variety of processes. For example, the coating element source can be dissolved in an organic solvent or water. The coating element sources include metal alkoxide, salt or oxide (e.g., aluminum isopropoxide or magnesium methoxide). Spinel cathode materials are then dispersed in the coating solution. The mixture is stirred until the organic solvent is completely evaporated. If necessary, a flushing gas ($CO_2$ or moisture-free inert gas) may be used to help facilitate evaporation of the solvent in the coating solution. The dried, coated material is then heat-treated at a temperature ranging from about 100° C. to about 500° C.

A $TiO_2$ coating can be applied to spinel powders by hydroxylation of tetra-n-butyl titanate (TBT). Thus, for example, the titanate can be reacted with LiOH to precipitate the titanium hydroxide onto the spinel powder. The coated material can be heat-treated at 100 to about 400° C. to yield spinel particles with the desired oxide coating.

A sol-gel process may also be employed in the coating of the spinel. The coating materials including M-ethylhexanate-diisopropoxide (M=Zr, Al, Ti, B, Si) and tin ethylhexanoisopropoxide can be dissolved in alcohol (e.g., 2-propanol or isopropanol). The cathode materials are then mixed with the coating solution and annealed at from about 100° C. to about 500° C. Alternatively, a coating solution can be prepared by dissolving ethyl silicate in ethanol and water. Spinel powder is immersed in the coating solution, stirred, dried at 110° C., and then is calcined at from about 200° C. to about 500° C.

The process of coating spinel with $AlPO_4$ can be carried out by dissolving aluminum nitrate and ammonium phosphate in water until a light white suspension solution (the $AlPO_4$ nano-particle solution) is observed. Spinel cathode powder is then added to the coating solution and mixed. The slurry can be dried and annealed at from about 100° C. to about 500° C.

Colloidal suspensions may also be used to coat spinel with metal oxides. For example, the spinel powders can be coated using a 4 wt % (~0.3 mol %) colloidal $ZrO_2$ suspension. The spinel particles are immersed and stirred in the $ZrO_2$ suspension for about 1 h, followed by evaporation of the nascent liquid at 75° C. Thereafter, the products can be heated at about 200 to 400 or 500° C.

Alternatively, the $ZrO_2$ coating of spinel can be carried out by using two different coating solutions (zirconium oxide+ polymeric precursor or an aqueous solution of zirconium nitrate). Spinel could be mixed with the coating solutions until the mixture is dry. Then the mixture could be heated at 100° C. to evaporate the solvents in the coating solutions. The dried mixture could be heat-treated at 200-500° C.

A $ZnO_2$ coating can be applied to the spinel by dissolving zinc acetate in water, followed by adding the spinel powder, and thoroughly mixing for about 4 h at room temperature. After drying, the coated powder is heated at 120° C., and is further calcined at about 200° C. to about 400° C.

Finally, spinel can be coated using a co-precipitation process. Spinel powder is dispersed into a $NaHCO_3$ solution and ultrasonically agitated. The suspension is then stirred mechanically while $Al_2(SO_4)_3$ solution is added drop wise to it. In this way, $Al(OH)_3$ is precipitated onto the spinel particle surface. The final powder is filtered, washed, and dried. The dried powder is heated in air at about 200° C. to about 600° C.

Stabilized electrodes comprised of blends of materials and electrochemical devices employing the same are also within the scope of the present technology. For example, the cathode can include a blend of spinel and $Li_{1+x}Ni_\alpha Mn_\beta Co_\gamma Met'_\delta O_{2-z}F_{z'}$, wherein Met' is Mg, Zn, Al, Ga, B, Zr, or Ti; and wherein $0 \le x' \le 0.4$, $0 \le \alpha \le 1$, $0 \le \beta \le 1$, $0 \le \gamma \le 1$, $0 \le \delta \le 0.4$, and $0 \le z' \le 0.4$. The ratio of spinel to $Li_{1+x}Ni_\alpha Mn_\beta Co_\gamma Met'_\delta O_{2-z}F_{z'}$ is typically from about 0.5 to about 60 wt %. Suitable cathodes can also include a blend of olivine or carbon coated olivine and $Li_{1+x}Ni_\alpha Mn_\beta Co_\gamma Met'_\delta O_{2-z}F_{z'}$, wherein Met' is Mg, Zn, Al, Ga, B, Zr, or Ti; and wherein $0 \le x \le 0.4$, $0 \le \alpha \le 1$, $0 \le \beta \le 1$, $0 \le \gamma \le 1$, $0 \le \delta \le 0.4$, and $0 \le z \le 0.4$. As before, the ratio of olivine or carbon-coated olivine to $Li_{1+x}Ni_\alpha Mn_\beta Co_\gamma Met'_\delta O_{2-z}F_{z'}$ can be from about 0.5 to about 98 wt %.

Such mixed electrodes can be used with any of the electrochemical devices described herein, including those in which the alkali metal salt of the electrolyte is $Li(C_2O_4)BF_2$, $Li[(C_2O_4)_2B]$, or mixtures thereof as well as those utilizing the electrode stabilizing additives described herein.

The porous separator may be made from materials well known to those skilled in the art. Typically, the porous separator comprises polypropylene, polyethylene, or a multilayer laminate of polypropylene and polyethylene.

Thus, in accordance with one embodiment, the electrochemical device of the present technology includes a spinel, olivine, or carbon-coated olivine cathode; a graphite or amorphous carbon anode; and a substantially nonaqueous electrolyte comprising an alkali metal salt that is $Li(C_2O_4)BF_2$ or $Li[(C_2O_4)_2B]$; a polar aprotic solvent that is ethyl acetate, propyl acetate, ethylene carbonate, propylene carbonate, dimethyl carbonate, diethyl carbonate, ethyl methyl carbonate, dimethyl ether, gamma butyrolactone, or a mixture of any two or more thereof; and a stabilizing additive selected from any of the triazinane triones or bicyclic compounds including a succinic anhydride described herein, including, but not limited to, TTT and ODH.

In some embodiments of electrochemical devices of the present technology, the cathode is spinel, olivine, or carbon coated olivine and the alkali metal salt of the electrolyte includes $Li(C_2O_4)BF_2$, $Li[(C_2O_4)_2B]$, or mixtures thereof. In some embodiments, the at least one stabilizing additive selected from any of the triazinane triones or bicyclic compounds including a succinic anhydride described herein. The electrochemical device may include additional stabilizing additives in the electrolyte selected from 3,9-divinyl-2,4,8,10-tetraoxaspiro[5.5]undecane, 3,9-divinyl-2,4,8-trioxaspiro[5.5]undecane, 3,9-divinyl-2,4-dioxaspiro[5.5]undecane, 3,9-diethylidene-2,4,8,10-tetraoxaspiro[5.5]undecane, 3,9-diethylidene-2,4,8-trioxaspiro[5.5]undecane, 3,9-diethylidene-2,4-dioxaspiro[5.5]undecane, 3,9-dimethylene-2,4,8,10-tetraoxaspiro[5.5]undecane, 3,9-divinyl-1,5,7,11-tetraoxaspiro[5.5]undecane, 3,9-dimethylene-1,5,7,11-tetraoxaspiro[5.5]undecane, 3,9-diethylidene-1,5,7,11-tetraoxaspiro[5.5]undecane, or a mixture of any two or more thereof. In any of these embodiments, the cathode can include a surface coating of a metal oxide as described herein.

While not wishing to be limited by any theory, it is believed that electrochemical devices of the present technology exhibit enhanced performance due to the stabilizing additives present in the non-aqueous electrolytes. Thus, it is believed that the additives protect the electrodes from chemical attack, thereby lessening or preventing subsequent performance degradation. Specifically, it is believed that during initial formation of the electrochemical device, the additive forms a protective film on the surface of the positive electrode (cathode), and can also form a protective film on the surface of the negative electrode (anode). The passivating film prevents $Mn^{2+}$ and $Fe^{2+}$ ions from dissolving in the electrolyte and stabilizes the cell in general. Where a passivating film is formed on the anode, the film also lessens or prevents the reduction of $Mn^{2+}$ ions (from spinel cathodes) and $Fe^{2+}$ ions (from olivine cathodes) at the anode surface. During the film-forming process, additives of the present technology may be oxidized, or oxidized and polymerized. Additives of the present technology typically have an oxidation potential ranging from about 1.5V and about 6.5V $Li/Li^+$.

In another aspect, the present technology provides new compounds for use as stabilizing additives in the present electrolytes. The compounds include compounds of Formulas I and II:

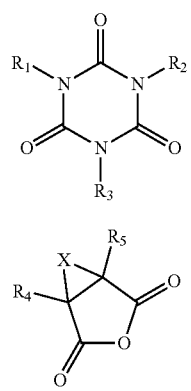

wherein:
$R^1$, $R^2$, $R^3$, $R^4$ and $R^5$ are independently H, F, Cl, Br, CN, $NO_2$, a substituted or unsubstituted alkyl, alkoxyalkyl, alkenyl or alkynyl group, organophosphate, an ester group, a substituted or unsubstituted siloxyalkyl group, a substituted or unsubstituted silylalkyl group, a substituted or unsubstituted epoxy or epoxyalkyl group, a substituted or unsubstituted carbonate group, a substituted or unsubstituted ethylene carbonate group, a substituted or unsubstituted vinyl carbonate group, or a substituted or unsubstituted vinyl ethylene carbonate group; provided that at least one of $R^1$, $R^2$, and $R^3$ is not H, methyl, or allyl;

X is selected from a group of Formula IIIA, IIIB, IIIC, IIID, or IIIE

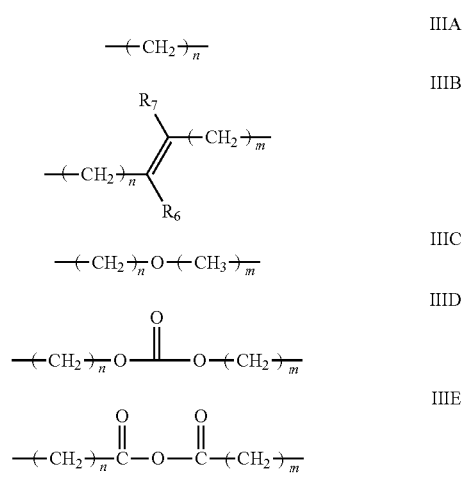

$R^6$ and $R^7$ are independently H, F, Cl, Br, a substituted or unsubstituted alkyl, alkenyl, or alkynyl group;

n is an integer from 1 to 6 for formula IIIA and from 0 to 4 for formulas IIIB-IIIE; and m is an integer from 0 to 4 such that the sum of n and m is not greater than 4;

provided that when X has formula IIIA and $R^4$ and $R^5$ are both H, then n is an integer from 3 to 6.

In some embodiments of the compounds of Formulas I and II, $R^1$, $R^2$, $R^3$, $R^4$ and $R^5$ may be independently selected from H, F, Cl, Br, I, an unsubstituted alkyl or alkenyl group, a haloalkyl group, an epoxyalkyl group, or an alkyl, alkenyl or alkoxyalkyl group substituted with a substituent selected from the group consisting of ethylene carbonate, vinyl ethylene carbonate, vinyl carbonate, and an ester. In some embodiments, the ester is acrylate. In other embodiments, $R^1$, $R^2$, $R^3$, $R^4$ and $R^5$ may be independently selected from H, F, Cl, Br, I, an unsubstituted $C_1$-$C_4$ alkyl group, an unsubstituted $C_2$-$C_6$ alkenyl group, an unsubstituted $C_2$-$C_6$ alkynyl group, a $C_1$-$C_4$ alkyl group substituted with a $C_2$-$C_6$ ester group, a $C_4$-$C_8$ silylalkyl group, a $C_4$-$C_8$ siloxylalkyl group, a $C_2$-$C_4$ alkoxyalkyl group substituted with an ethylene carbonate group, or a $C_2$-$C_{10}$ epoxy or epoxyalkyl group. In some embodiments, $R^1$, $R^2$, $R^3$, $R^4$ and $R^5$ are independently selected from the group consisting of methyl, ethyl, n-propyl, iso-propyl, n-butyl, sec-butyl, tert-butyl, vinyl, 2-propenyl, 3-butenyl, acetylenyl and 2-propynyl, 3-butynyl. $R^1$, $R^2$, and $R^3$ may be the same so long as at least one of $R^1$, $R^2$, and $R^3$ is not H, methyl, or allyl. $R^4$ and $R^5$ may be the same (e.g., both H), provided that when X has formula IIIA and $R^4$ and $R^5$ are both H, then n is an integer from 3 to 6.

Representative compound of Formulas I and II include the following:
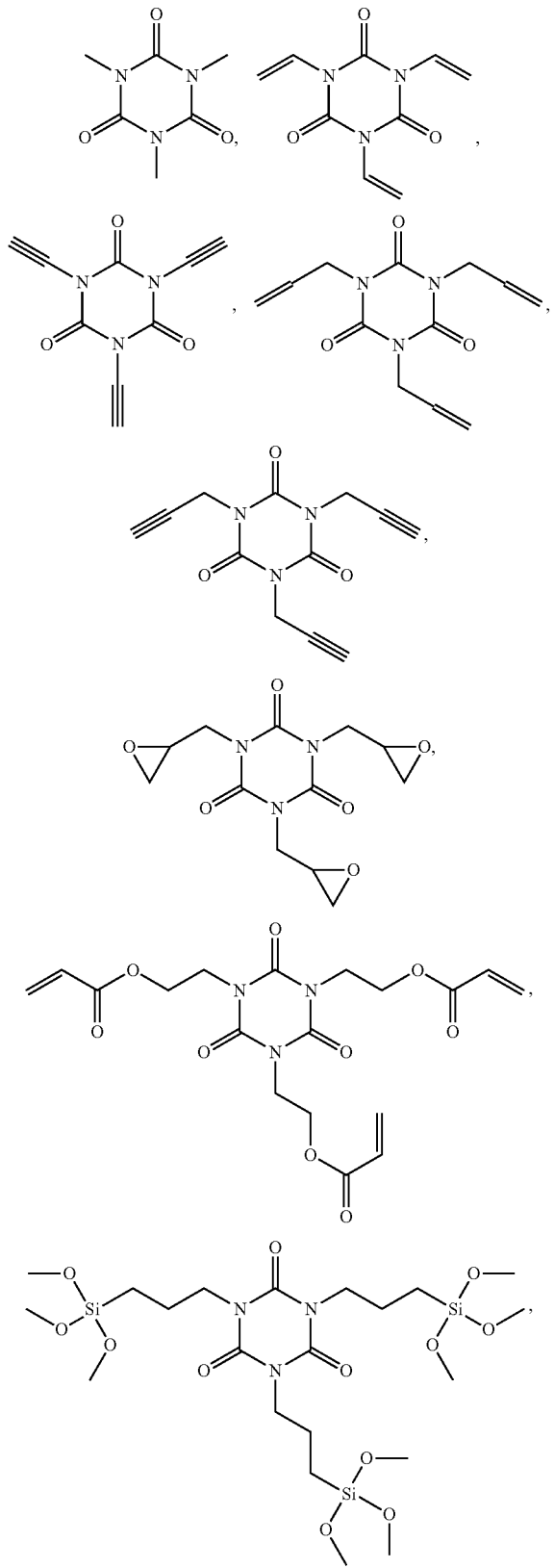
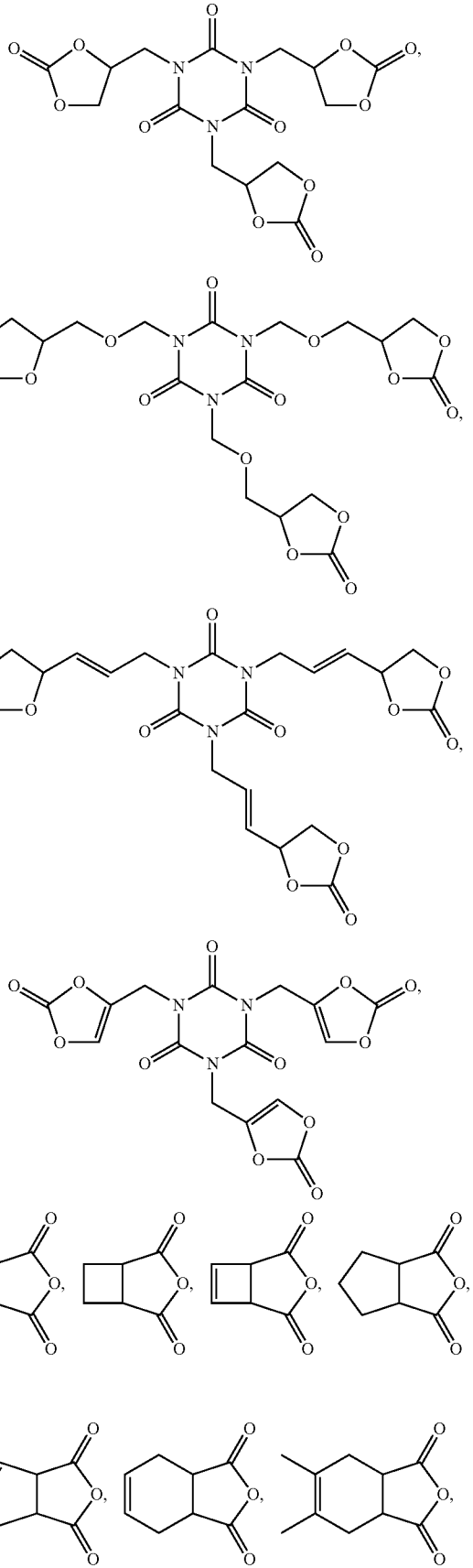

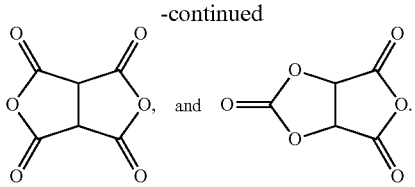

In some embodiments, the compound of Formulas I and II include the following:

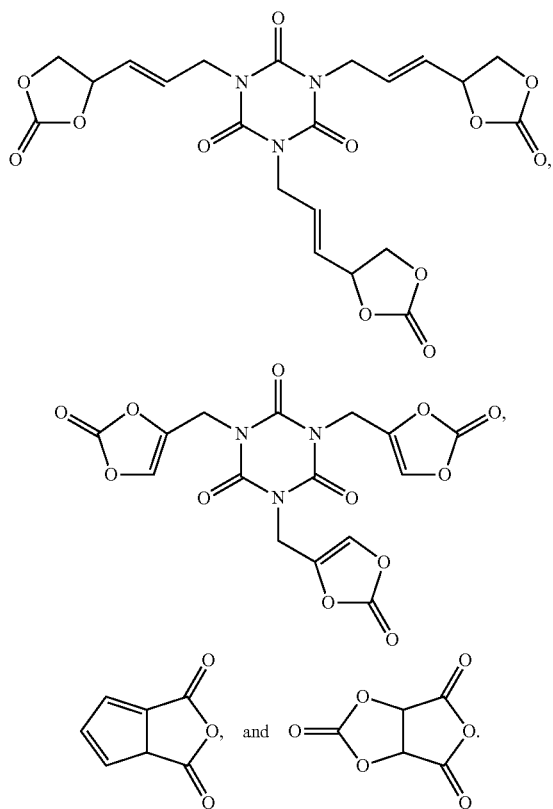

The synthesis of representative compounds of Formulas I and II may be carried out using known procedures or can be readily adapted from them by those skilled in the art based on the following references: "N-Heterocyclic carbenes as highly efficient catalysts for the cyclotrimerization of isocyanates," Duong, H. A. et al., *Organic Letters*, 6(25), 4679-4681, 2004; "Bis(ethyl-3-oxobutanolato-O1,O3)-bis(2-propanolato)titanium (Tyzor DC) as a reactant and catalyst in the trimerization of 2-isocyanatoethyl methacrylate (IEM)," Graham, J. C. et al., *Catalysis Letters*, 3(5-6), 413-20, 1989; "A process for preparing triglycidyl isocyanurate," Xia, E. et al. *Faming Zhuanli Shenqing Gongkai Shuomingshu*, CN Patent No. 101643452, 10 Feb. 2010; "Synthesis and N-methylation of tetrabutylammonium isocyanurate," Havet, J.-L. et al., *Tetrahedron Letters*, 44(23), 4399-4402, 2003; "Process for the production of isocyanatosilane and silylisocyanurate," Childress, R. S. and Burns, P. J. in U.S. Pat. Appl. Publ., 2006/276644, 07 Dec. 2006; "Potent non-nitrile dipeptidic dipeptidyl peptidase IV inhibitors," Simpkins, L. M. et al. *Bioorganic & Medicinal Chemistry Letters*, 17(23), 6476-6480, 2007; "Synthesis of the constrained glutamate analogs (2S,1'R,2'R)- and (2S,1'S,2'S)-2-(2'-carboxycyclobutyl) glycines L-CBG-II and L-CBG-I by enzymatic transamination," Gu, X. et al. from *Tetrahedron Letters*, 47(2), 193-196, 2005; "Fate of the Intermediate Diradicals in the Caldera: Stereochemistry of Thermal Stereomutations, (2+2) Cycloreversions, and (2+4) Ring-Enlargements of cis- and trans-1-Cyano-2-(E and Z)-propenyl-cis-3,4-dideuteriocyclobutanes," von Doering, W. et al. *J. Am. Chem. Soc.*, 124(39), 11642-11652, 2002; "Reactivity patterns in the rhodium carbenoid induced tandem cyclization-cycloaddition reaction," Padwa, A. et al. from *J. of Org. Chem.*, 54(4), 817-24, 1989; "(E)-1-Trimethylsilyl-1,3-butadiene," Fleming, I. from e-EROS Encyclopedia of Reagents for Organic Synthesis, 2001. Each of the previous references are incorporated herein by reference in their entirety and for all purposes.

The following terms are used throughout as defined below.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); alkoxy, alkenoxy, and aralkyloxy groups; carbonyls (=O); carboxyls (—COOH); esters; urethanes; sulfides; sulfoxides; sulfones; sulfonyls; sulfonamides; amines; hydrazones; amides; amidines; enamines; isocyanates (—N=C=O); isothiocyanates (—N=C=S); nitro groups (i.e., —$NO_2$); nitriles (i.e., —CN); and the like.

Substituted ring groups such as substituted cycloalkyl, aryl, and heterocyclyl groups also include rings and fused ring systems in which a bond to a hydrogen atom is replaced with a bond to a carbon atom. Therefore, substituted cycloalkyl, aryl, and heterocyclyl groups may also be substituted with substituted or unsubstituted alkyl, alkenyl, and alkynyl groups as defined below.

Alkyl groups include straight chain and branched chain saturated hydrocarbon groups having from 1 to 20 carbons unless indicated otherwise. For example, a $C_{1-6}$ alkyl group includes alkyl groups with 1, 2, 3, 4, 5, or 6 carbon atoms. In some embodiments, an alkyl group has from 1 to 14 carbon atoms, from 1 to 12 carbon atoms, from 1 to 10 carbons, from 1 to 8, 1 to 6, or 1, 2, 3 or 4 carbon atoms. Examples of straight chain alkyl groups include groups such as methyl, ethyl, n-propyl, n-butyl, n-pentyl, n-hexyl, n-heptyl, and n-octyl, n-decyl, n-dodecyl and n-tetradecyl groups. Examples of branched chain alkyl groups include, but are not limited to, isopropyl, iso-butyl, sec-butyl, tert-butyl, neopentyl, isopentyl, and 2,2-dimethylpropyl groups. Representative substituted alkyl groups may be substituted one or more times with substituents such as those listed above, and in some embodiments have 1, 2, 3, 4, 5 or 6 substituents.

Alkylene groups are alkyl groups, as defined herein, which are divalent; i.e., they have two points of attachment to a compound of the present technology. Representative alkylene groups include but are not limited to —$CH_2$—, —$CH_2CH_2$—, —$CH(CH_3)CH_2$—.

Cycloalkyl groups include mono-, bi- or tricyclic alkyl groups having from 3 to 12 carbon atoms in the ring(s), or, in some embodiments, 3 to 10, 3 to 8, or 3, 4, 5, or 6 carbon atoms. Exemplary monocyclic cycloalkyl groups include, but are not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Bi- and tricyclic ring systems include both bridged cycloalkyl groups and fused rings, such as, but not limited to, adamantyl, decalinyl, and the like. Cycloalkyl groups may be unsubstituted or substituted by the same substituents and in the same number as alkyl groups are.

Alkenyl groups are straight chain, branched or cyclic alkyl groups having 2 to 14 carbon atoms, and further including at least one double bond between adjacent carbon atoms. In some embodiments alkenyl groups have from 2 to 12, 2 to 10, 2 to 8 or from 2 to 6 carbon atoms. Alkenyl groups include, for instance, vinyl, propenyl, 2-butenyl, 3-butenyl, isobutenyl, cyclohexenyl, cyclopentenyl, cyclohexadienyl, butadienyl, pentadienyl, and hexadienyl groups among others. Alkenyl groups may be substituted similarly to alkyl groups. Divalent alkenyl groups, i.e. alkenyl groups with two points of attachment, include but not limited to CH—CH=CH$_2$, C=CH$_2$, or C=CHCH$_3$.

Alkynyl groups are straight chain or branched alkyl groups having 2 to 14 carbon atoms, and further including at least one triple bond between adjacent carbon atoms. In some embodiments alkynyl groups have from 2 to 12, 2 to 10, 2 to 8 or from 2 to 6 carbon atoms. Exemplary alkynyl groups include, but are not limited to, ethynyl, propynyl, and butynyl groups. Alkynyl groups may be substituted similarly to alkyl groups. Representative substituted alkynyl groups may be substituted 1 or more times with substituents such as those listed above, and in some embodiments have 1, 2, 3, 4, 5 or 6 substituents.

Aryl groups are cyclic aromatic hydrocarbons that do not contain heteroatoms. Aryl groups herein include monocyclic, bicyclic and tricyclic ring systems. Thus, aryl groups include, but are not limited to, phenyl, azulenyl, heptalenyl, biphenyl, fluorenyl, phenanthrenyl, anthracenyl, indenyl, indanyl, pentalenyl, and naphthyl groups. Aryl groups contain 6-14 carbons in the ring portions of the groups. In some embodiments, aryl groups have from 6 to 12 or even 6-10 carbon atoms in the ring portions of the groups. In some embodiments, the aryl groups are phenyl or naphthyl. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

Aralkyl groups are alkyl groups as defined above in which a hydrogen or carbon bond of an alkyl group is replaced with a bond to an aryl group as defined above. In some embodiments, aralkyl groups contain 7 to 16 carbon atoms, 7 to 14 carbon atoms, or 7 to 10 carbon atoms. Substituted aralkyl groups may be substituted at the alkyl, the aryl or both the alkyl and aryl portions of the group. Representative aralkyl groups include but are not limited to benzyl and phenethyl groups and fused (cycloalkylaryl)alkyl groups such as 4-indanylethyl. Representative substituted aralkyl groups may be substituted one or more times with substituents such as those listed above.

Alkoxy groups are hydroxyl groups (—OH) in which the bond to the hydrogen atom is replaced by a bond to a carbon atom of a substituted or unsubstituted alkyl group as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Representative substituted alkoxy groups may be substituted one or more times with substituents such as those listed above, and in some embodiments have 1, 2, 3, 4, 5 or 6 substituents.

The terms "aryloxy" and "arylalkoxy" refer to, respectively, a substituted or unsubstituted aryl group bonded to an oxygen atom and a substituted or unsubstituted aralkyl group bonded to the oxygen atom at the alkyl. Examples include but are not limited to phenoxy, naphthyloxy, and benzyloxy. Representative substituted aryloxy and arylalkoxy groups may be substituted one or more times with substituents such as those listed above, and in some embodiments have 1, 2, 3, 4, 5 or 6 substituents.

Alkoxyalkyl groups are alkyl groups as defined herein in which an internal carbon atom in the chain has been replaced with an oxygen. Thus, alkoxyalkyl groups do not include alkyl groups substituted with a hydroxyl group. Representative alkoxyalkyl groups include ethoxymethyl, methoxyethyl, ethoxyethyl, isopropoxymethyl, and the like. Alkoxyalkyl groups may be substituted one or more times with substituents such as those listed above, and in some embodiments have 1, 2, 3, 4, 5 or 6 substituents.

The term "amine" (or "amino") as used herein refers to —NHR$^{35}$ and —NR$^{36}$R$^{37}$ groups, wherein R$^{35}$, R$^{36}$ and R$^{37}$ are independently hydrogen, or a substituted or unsubstituted alkyl, alkenyl, alkynyl, cycloalkyl, aryl, or aralkyl group as defined herein. In some embodiments, the amine is NH$_2$, methylamino, dimethylamino, ethylamino, diethylamino, propylamino, isopropylamino, phenylamino, or benzylamino.

The term "amide" (or "amido") includes C- and N-amide groups, i.e., —C(O)NR$^{31}$R$^{32}$, and —NR$^{31}$C(O)R$^{32}$ groups, respectively. R$^{31}$ and R$^{32}$ are independently hydrogen, or a substituted or unsubstituted alkyl, alkenyl, alkynyl, cycloalkyl, aryl, and aralkyl group as defined herein. Amido groups therefore include but are not limited to carbamoyl groups (—C(O)NH$_2$) and formamide groups (—NHC(O)H).

The term "amidine" refers to —C(NR$^{47}$)NR$^{48}$R$^{49}$ and —NR$^{47}$C(NR$^{48}$)R$^{49}$, wherein R$^{47}$, R$^{48}$, and R$^{49}$ are each independently hydrogen, or a substituted or unsubstituted alkyl, cycloalkyl, alkenyl, alkynyl, aryl or aralkyl group as defined herein.

The term "carboxylate" as used herein refers to a —COOH group.

The term "substituted or unsubstituted carbonate group" refers to carbonate groups having the formula R$^{70}$OC(O)OR$^{71}$, wherein R$^{70}$ and R$^{71}$ are independently a substituted or unsubstituted alkyl or alkenyl group, or R$^{70}$ and R$^{71}$ together are a substituted or unsubstituted ethylene or ethenylene group (i.e., —CH$_2$CH$_2$— or —CH=CH—) and the carbonate is cyclic. As a substituent on another compound, e.g., additives of the present technology, the carbonate group may be attached through its R$^{70}$ and R$^{71}$ groups. Representative substituted or unsubstituted carbonate groups include but are not limited to ethyl methyl carbonate, ethylene carbonate (1,3-dioxolan-2-one), vinyl ethylene carbonate (4-vinyl-1,3-dioxolan-2-one) and vinyl carbonate (1,3-dioxol-2-one).

The term "enamine" refers to —C(R$^{54}$)=C(R$^{55}$)NR$^{56}$R$^{57}$ and —NR$^{54}$C(R$^{55}$)=C(R$^{56}$)R$^{57}$, wherein R$^{54}$, R$^{55}$, R$^{56}$ and R$^{57}$ are each independently hydrogen, a substituted or unsubstituted alkyl, cycloalkyl, alkenyl, alkynyl, aryl aralkyl, heterocyclyl or heterocyclylalkyl group as defined herein.

The term "ester" as used herein refers to —COOR$^{30}$ and —OC(O)R$^{30}$ groups. R$^{30}$ is a substituted or unsubstituted alkyl, cycloalkyl, alkenyl, alkynyl, aryl or aralkyl group as defined herein.

The term "hydrazone" as used herein refers to =NNR$^{60}$R$^{61}$. R$^{60}$ and R$^{61}$ are independently selected from H, and substituted or unsubstituted alky, cycloalkyl, alkenyl, alkynyl, aryl, or aralkyl groups.

The term "olivine" refers to iron-based olivine such as, e.g., LiFe$_{1-z}$Met"$_y$PO$_{4-m}$X$_n$, wherein Met" is Al, Mg, Ti, B, Ga, Si, Ni, Mn or Co; X is S or F; and wherein 0≤x≤0.3; 0≤y≤0.5, 0≤z≤0.5, 0≤m≤0.5 and 0≤n≤0.5.

The term "organophosphate" refers to —OP(O)(OR$^{40}$)$_2$ groups where each R$^{40}$ group is independently H or an alkyl or cycloalkyl group, so long as at least one R$^{40}$ is not hydrogen.

The term "polar aprotic solvent" refers to liquids that lack exchangeable hydrogens, but have functional groups that impart polarity (e.g., as evidenced by dielectric constant) to the solvent. Classes of polar aprotic solvents include, e.g., cyclic carbonic acid esters, linear carbonic acid esters, phosphoric acid esters, oligoether substituted siloxanes/silanes, cyclic ethers, chain ethers, lactone compounds, chain esters, nitrile compounds, amide compounds, sulfone compounds and the like.

The term "silylalkyl group" refers to an alkyl group as defined herein substituted with one or more silyl groups of the formula —Si(R$^{50}$)$_3$, wherein R$^{50}$ is selected from an alkyl, cycloalkyl, alkenyl, aryl, or aralkyl group and one of the R$^{50}$ groups may itself be substituted with another silyl groups. In some embodiments, the silylalkyl is a $C_4$-$C_8$ silylalkyl.

The term "siloxyalkyl" refers to an alkyl group substituted with one or more siloxy groups having the formula —OSi(R$^{60}$)$_3$, wherein R$^{60}$ is selected from an alkyl, cycloalkyl, alkenyl, aryl, or aralkyl group and one of the R$^{60}$ groups may itself be substituted with another siloxy group. In some embodiments the siloxyalkyl is a $C_4$-$C_8$ siloxylalkyl.

The term "sulfonamido" includes S- and N-sulfonamide groups, i.e., —SO$_2$NR$^{38}$R$^{39}$ and —NR$^{38}$SO$_2$R$^{39}$ groups, respectively. R$^{38}$ and R$^{39}$ are independently hydrogen, or a substituted or unsubstituted alkyl, alkenyl, alkynyl, cycloalkyl, aryl, or aralkyl group as defined herein. Sulfonamido groups therefore include but are not limited to sulfamoyl groups (—SO$_2$NH$_2$).

The term "thiol" refers to —SH groups, while sulfides include —SR$^{41}$ groups, sulfoxides include —S(O)R$^{42}$ groups, sulfones include —SO$_2$R$^{43}$ groups, and sulfonyls include —SO$_2$OR$^{44}$. R$^{41}$, R$^{42}$, R$^{43}$, and R$^{44}$ are each independently a substituted or unsubstituted alkyl, cycloalkyl, alkenyl, alkynyl, aryl, or aralkyl group as defined herein.

Urethane groups include N- and O-urethane groups, i.e., —NR$^{33}$C(O)OR$^{34}$ and —OC(O)NR$^{33}$R$^{34}$ groups, respectively. R$^{33}$ and R$^{34}$ are independently a substituted or unsubstituted alkyl, alkenyl, alkynyl, cycloalkyl, aryl or aralkyl group as defined herein. R$^{33}$ may also be H.

Spirocyclic hydrocarbons include ring systems comprising carbon and hydrogen and having two or more rings in which at least two of the rings are joined at a single carbon.

The term "spinel" refers to manganese-based spinel such as, e.g., Li$_{1+x}$Mn$_{2-z}$Met$_y$O$_{4-m}$X$_n$, wherein Met is Al, Mg, Ti, B, Ga, Si, Ni, or Co; X is S or F; and wherein 0≤x≤0.3, 0≤y≤0.5, 0≤z≤0.5, 0≤m≤0.5 and 0≤n≤0.5.

The term "stabilizing additive" refers to additives to electrolytes for electrochemical devices (e.g., batteries) that stabilize one or both of the electrodes against degradation and extend cell cycle performance. Such stabilizing additives are believed to passivate the surface of the electrode, forming a thin film against further reaction between the electrode and the electrolyte.

One skilled in the art will readily realize that all ranges discussed can and do necessarily also describe all subranges therein for all purposes and that all such subranges also form part and parcel of this present technology. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present technology, thus generally described, will be understood more readily by reference to the following examples, which are provided by way of illustration and are not intended to be limiting of the present technology.

EXAMPLES

Example 1

One weight percent of 1,3,5-triallyl-1,3,5-triazine-2,4,6 (1H,3H,5H)-trione (TTT, available from SIGMA-ALDRICH) was added into an electrolyte of 1.2 M LiPF$_6$ in EC:EMC (ethyl methyl carbonate) (3:7 by wt %), which was tested in a 2032 coin cell using Li$_{1.2}$Ni$_{0.15}$Co$_{0.1}$Mn$_{0.55}$O$_2$/MCMB as electrodes. The cell was then cycled at 55° C. for 2 cycles at C/10 rate between 3~4 V. Another cell using straight electrolyte without additive was also cycled under the same condition. The results then were converted into differential capacity profiles of each cell to demonstrate the SEI formation difference. However, by comparing the two cells' results, no obvious difference was observed in FIG. 1, which could mean additive TTT does decompose at a specific constant potential.

Example 2

Figure 2:
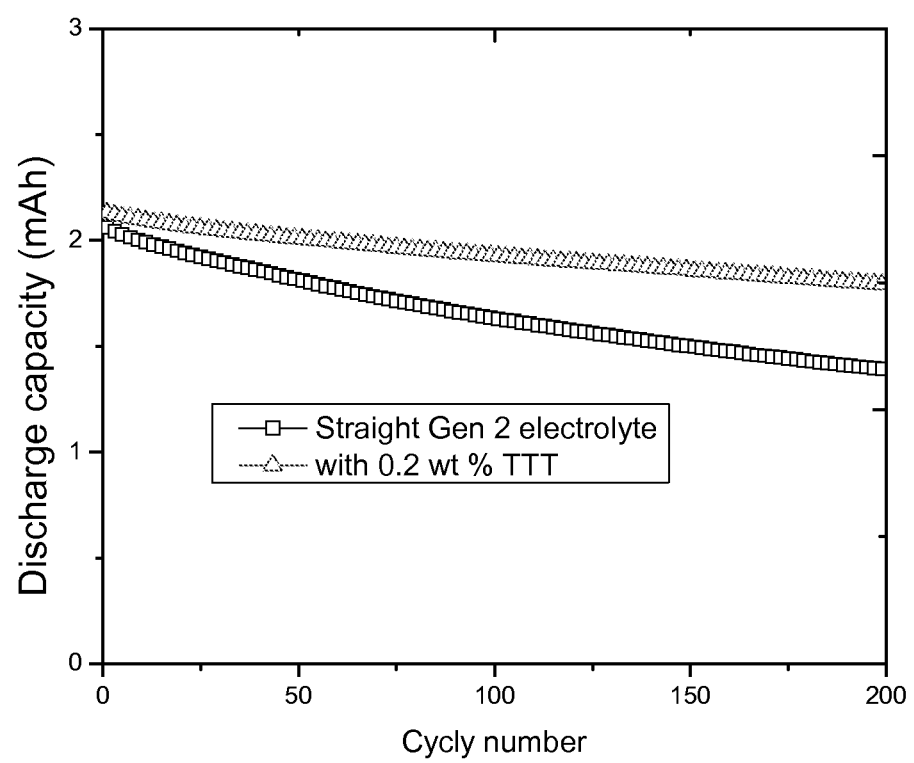
FIG. 2: Capacity retention profiles of MCMB-1028/$Li_{1.1}$ $[Ni_{1/3}Co_{1/3}Mn_{1/3}]_{0.9}O_2$ 2032 coin cells in Gen 2 electrolyte containing 0, 0.2 wt % TTT. The cells were cycled at 55° C. between 3~4 V with a constant current of 1 C (~2.0 mA).

The cells of example 1 were then optimized by reducing the concentration of 1,3,5-Triallyl-1,3,5-triazine-2,4,6(1H,3H, 5H)-trione from 1 weight percent to 0.2 weight percent in the aforementioned electrolyte. The cells containing electrolyte with and without additives at reduced concentration were then cycled at 55° C. for 200 cycles at 1 C rate between 3~4 V. The capacity retention profiles of each is shown in FIG. 2. As seen in the figure, with addition of additive TTT, the capacity retentions were much improved, especially for the electrolyte with 0.2 weight percent additive TTT. The results strongly indicate the additive participated into the SEI formation process and formed a more stable passivation film.

Example 3

Figure 3:
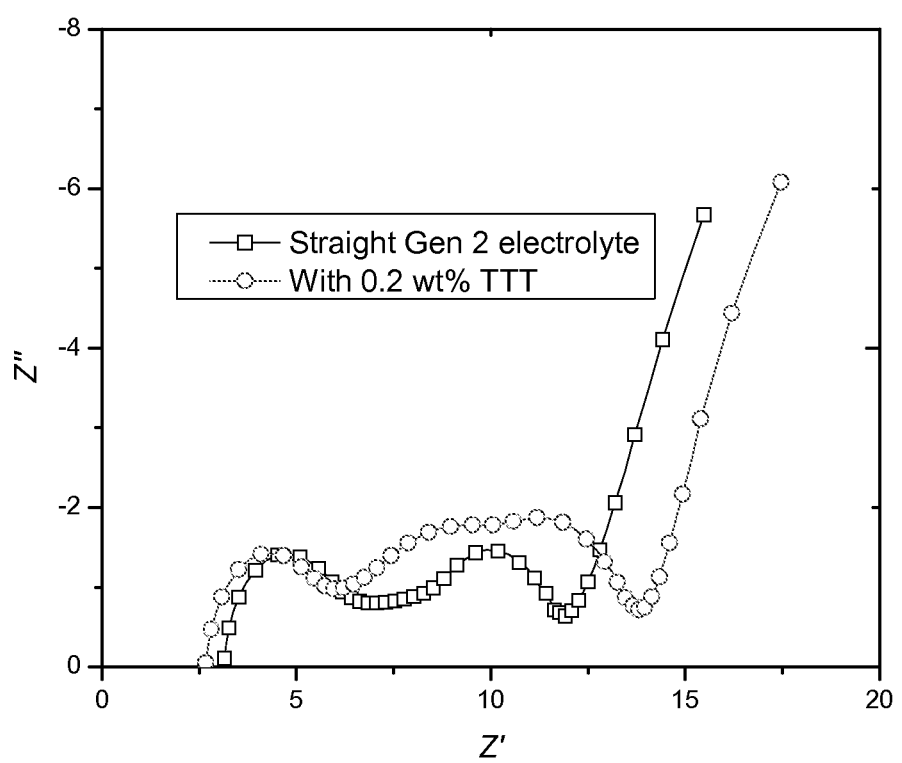
FIG. 3: AC impedance profile of MCMB-1028/$Li_{1.1}$ $[Ni_{1/3}Co_{1/3}Mn_{1/3}]_{0.9}O_2$ 2032 coin cells in Gen 2 electrolyte with 0 and 0.2 wt % additives. The cells were charged to 3.8 V at 55° C. with a constant current of 1 C (~2.0 mA).

The cells of example 2 were tested for AC impedance results before the 200 cycles at 55° C. The cells were charged to 3.8 V with a constant voltage method to assure the same SOC states. The AC impedance was collected over a frequency range of 10 mHz~1 MHz with Solartron Analytic 1470E cell test system coupled with 1454A Frequency Response Analyzer. As shown in FIG. 3, the interfacial impedance of the cell with additive is bigger than that of the cell without additive, suggesting the additive participating in the formation of the passivation film. The increase if the interfacial impedance is not favorable to the cell performance in terms of power, but the small extent still makes this additive promising for practice applications.

Example 4

Figure 4:
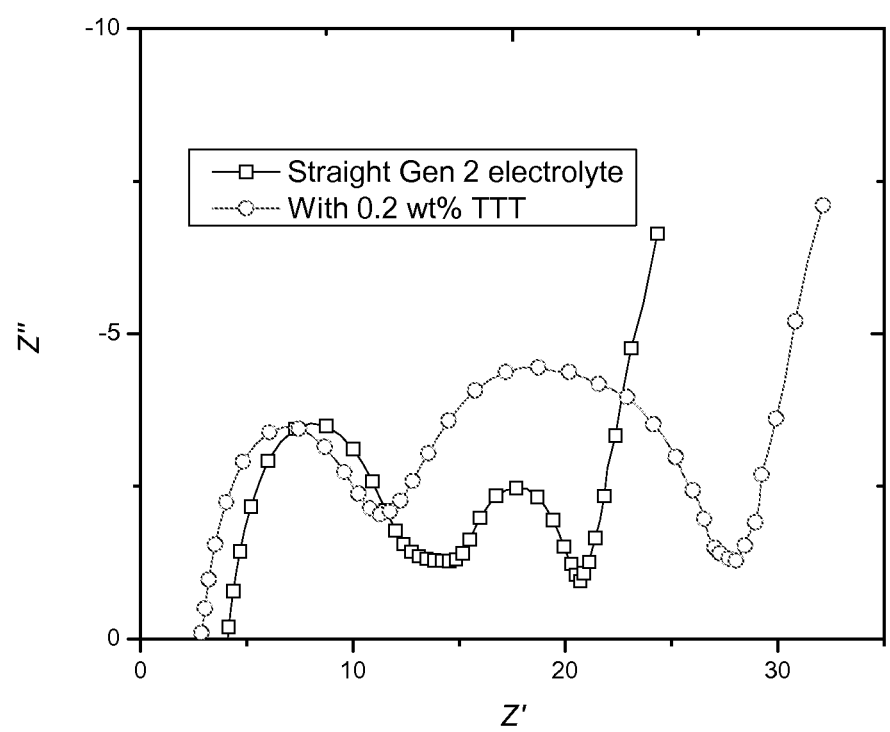
FIG. 4: AC impedance profile of MCMB-1028/$Li_{1.1}$ $[Ni_{1/3}Co_{1/3}Mn_{1/3}]_{0.9}O_2$ 2032 coin cells in Gen 2 electrolyte with 0 and 0.2 wt % additives. The cells were charged to 3.8 V after 200 cycles at 55° C. with a constant current of 1 C (~2.0 mA).

The cells of example 2 were tested for AC impedance results again after the 200 cycles at 55° C. The cells were charged to 3.8 V with a constant voltage method to assure the same SOC states. As shown in FIG. 4, the interfacial impedance of the cells with additive increased after 200 cycles and was still larger than that of the cell without additives.

Example 5

Figure 5:
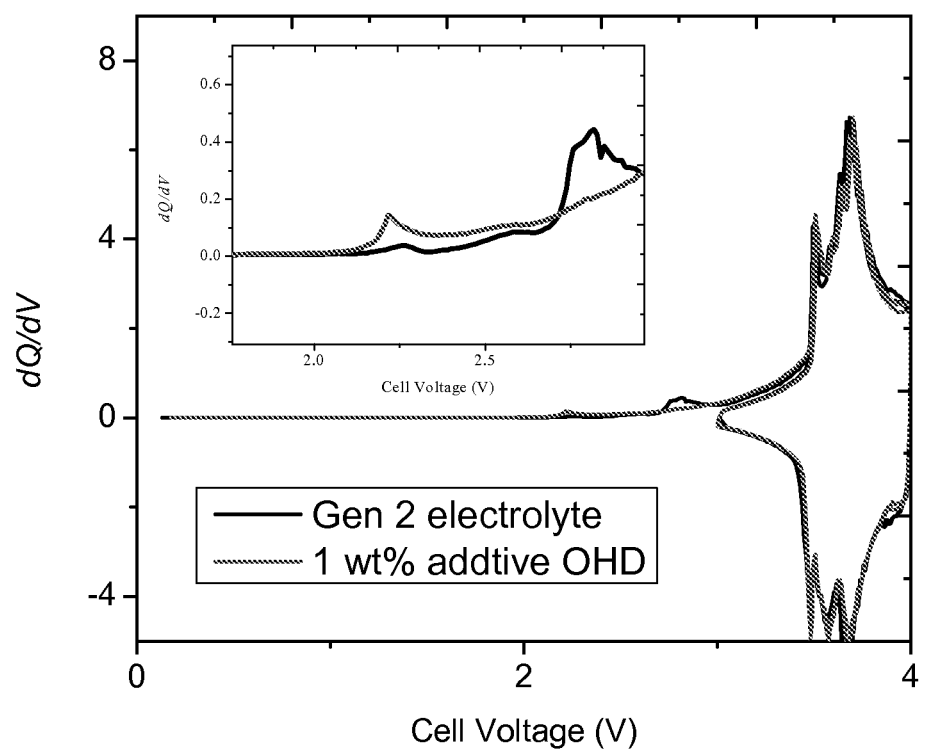
FIG. 5: Differential capacity profiles of the MCMB/$Li_{1.1}$ $[Ni_{1/3}Co_{1/3}Mn_{1/3}]_{0.9}O_2$ lithium-ion 2032 coin cells during the initial formation process in Gen 2 electrolyte with or without 1 wt % additives. The cells were cycled at 55° C. between 3~4 V with a constant current of 1 C (~2.0 mA).

One weight percent of 3-oxabicyclo[3.1.0]hexane-2,4-dione (OHD, available from SIGMA-ALDRICH), was added into an electrolyte of 1.2 M $LiPF_6$ in EC:EMC (3:7 by wt %), which was tested in a 2032 coin cell using $Li_{1.2}Ni_{0.15}Co_{0.1}Mn_{0.55}O_2$/MCMB as electrodes. The cell was then cycled at 55° C. for 2 cycles at C/10 rate between 3~4 V. Another cell using straight electrolyte without additive was also cycled under the same condition. The results then were converted into differential capacity profiles of each cell (see FIG. 5) to demonstrate the SEI formation difference. The profile of the cell with OHD exhibited a new peak at around 2.3 V and did not show the broad peak at 2.8 V resulted from EC. The results clearly indicated that additive OHD was involved into the formation process of passivation film on the electrodes surface.

Example 6

Figure 6:
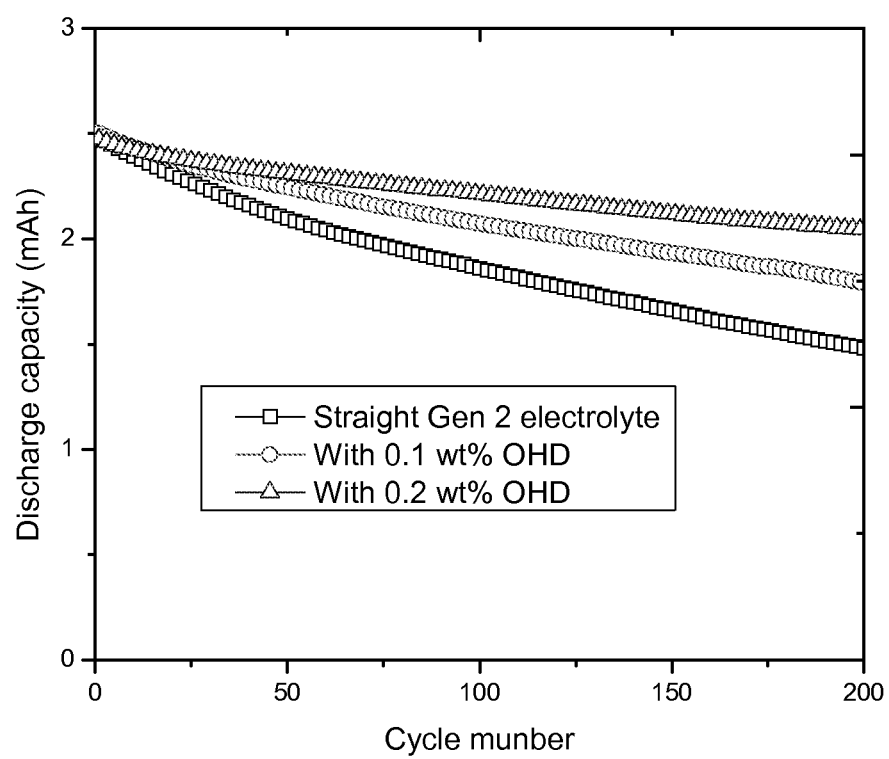
FIG. 6: Capacity retention profiles of MCMB-1028/$Li_{1.1}$ $[Ni_{1/3}Co_{1/3}Mn_{1/3}]_{0.9}O_2$ 2032 coin cells in Gen 2 electrolyte containing 0, 0.1, 0.2 wt % OHD. The cells were cycled at 55° C. between 2.7 and 4.2 V with a constant current of 1 C (~2.0 mA).

The cells of example 5 were then optimized by reducing the concentration of 3-oxabicyclo[3.1.0]hexane-2,4-dione trione from 1 weight percent to 0.1 and 0.2 weight percent in the aforementioned electrolyte. The cells containing electrolyte with and without additives at reduced concentration were then cycled at 55° C. for 200 cycles at 1 C rate between 2.7~4.2 V. The capacity retention profiles of them were shown in FIG. 2. As shown in the figure, with addition of additive OHD, the capacity retentions were much improved (see FIG. 6), especially for the electrolyte with 0.2 weight percent additive. The results strongly indicate the additive participated into the SEI formation process and formed a more stable passivation film.

Example 7

Figure 7:
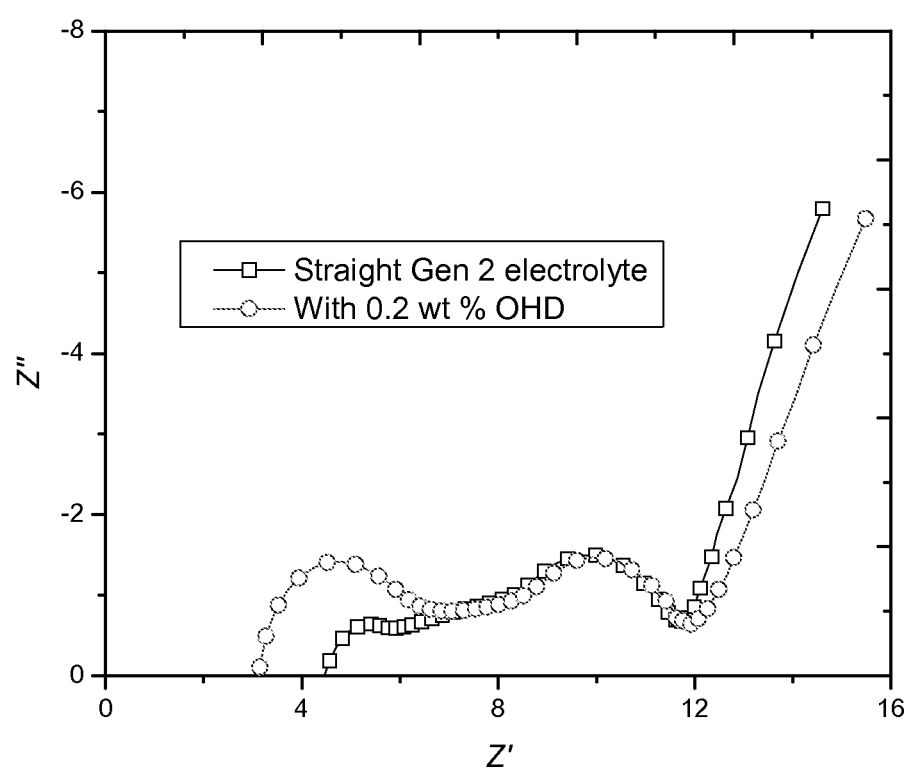
FIG. 7: AC impedance profile of MCMB-1028/$Li_{1.1}$ $[Ni_{1/3}Co_{1/3}Mn_{1/3}]_{0.9}O_2$ 2032 coin cells in Gen 2 electrolyte with 0 and 0.2 wt % additives. The cells were charged to 3.8 V before 200 cycles at 55° C. with a constant current of 1 C (~2.0 mA).

The cells of example 5 were tested for AC impedance results before the 200 cycles at 55° C. The cells were charged to 3.8 V with a constant voltage method to assure the same state of charge (SOC) states. As shown in FIG. 7, the interfacial impedance of the cells with and without additives were almost identical, suggesting OHD with low concentration will not affect the cell performance in terms of power output of the cell system.

Example 8

Figure 8:
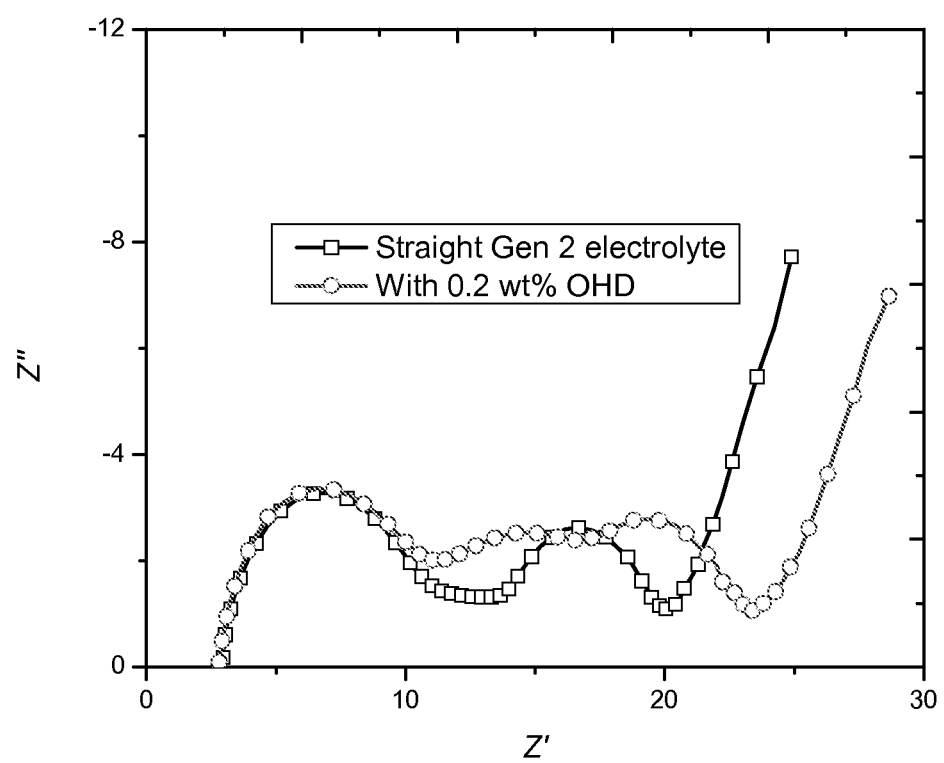
FIG. 8: AC impedance profile of MCMB-1028/$Li_{1.1}$ $[Ni_{1/3}Co_{1/3}Mn_{1/3}]_{0.9}O_2$ 2032 coin cells in Gen 2 electrolyte with 0 and 0.2 wt % additives. The cells were charged to 3.8 V after 200 cycles at 55° C. with a constant current of 1 C (~2.0 mA).

The cells of example 5 were tested for AC impedance results again after the 200 cycles at 55° C. The cells were charged to 3.8 V with a constant voltage method to assure the same SOC states. As shown in FIG. 8, the interfacial impedance of the cells with and without additives increased after 200 cycles at 55° C., and the extent of increase of the cell with additive was larger, suggesting with cycling the passivation film grew thicker.

We claim:
1. An electrolyte comprising:
an alkali metal salt;
a polar aprotic solvent; and
one or more stabilizing additives;
wherein:
at least one of the stabilizing additives is selected from the group consisting of:

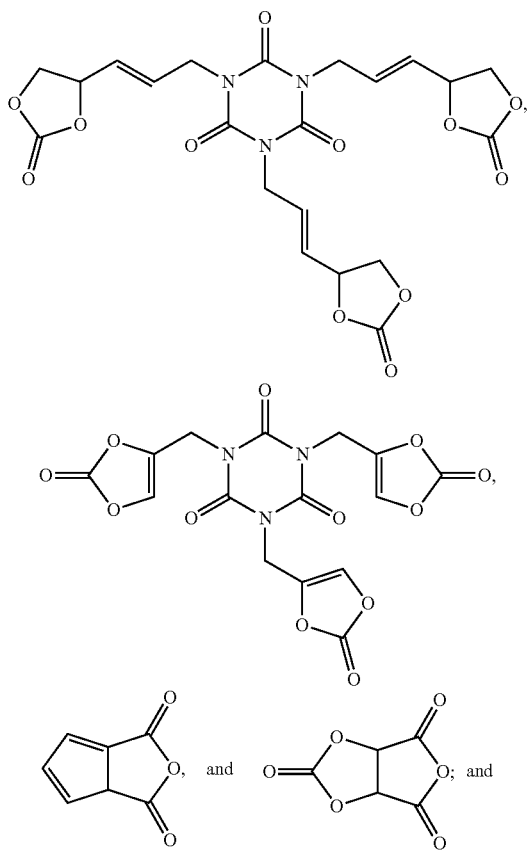

the electrolyte is substantially non-aqueous.
2. The electrolyte of claim 1, wherein a concentration of the additive in the electrolyte is from 0.0005 wt % to 50 wt %.
3. The electrolyte of claim 1, wherein the alkali metal salt is a lithium salt.
4. The electrolyte of claim 1, wherein the alkali metal salt is $Li[(C_2O_4)_2B]$,
$Li(C_2O_4)BF_2$, $LiClO_4$, $LiBF_4$, $LiAsF_6$, $LiPF_6$, $LiCF_3SO_3$, $Li(CF_3SO_2)_2N$, $Li(CF_3SO_2)_3C$,
$LiN(SO_2C_2F_5)_2$, lithium alkyl fluorophosphates, or a mixture of any two or more thereof.
5. The electrolyte of claim 1, wherein the polar aprotic solvent comprises ethylene carbonate, propylene carbonate, dimethyl carbonate; ethyl methyl carbonate; diethyl carbonate; methyl propyl carbonate; ethyl propyl carbonate; dipropyl carbonate;
bis(trifluoroethyl) carbonate; bis(pentafluoropropyl) carbonate; trifluoroethyl methyl carbonate; pentafluoroethyl methyl carbonate; heptafluoropropyl methyl carbonate;

perfluorobutyl methyl carbonate; trifluoroethyl ethyl carbonate; pentafluoroethyl ethyl carbonate; heptafluoropropyl ethyl carbonate; perfluorobutyl ethyl carbonate; fluorinated oligomers; dimethoxyethane; triglyme; dimethylvinylene carbonate; tetraethyleneglycol;

dimethyl ether; polyethylene glycols; sulfones; butyrolactone and mixtures of any two or more thereof.

6. An electrochemical device comprising a cathode;

an anode; and an electrolyte according to claim 1.

7. The electrochemical device of claim 6, wherein the device is a lithium secondary battery or capacitor; the cathode is a lithium metal oxide cathode; the anode is a carbon or lithium metal anode; and the anode and cathode are separated from each other by a porous separator.

8. A method of preparing the electrolyte of claim 1 comprising:

combining an alkali metal salt and one or more stabilizing additives in a polar aprotic solvent substantially free of water;

wherein:

at least one of the stabilizing additives is selected from the group consisting of:

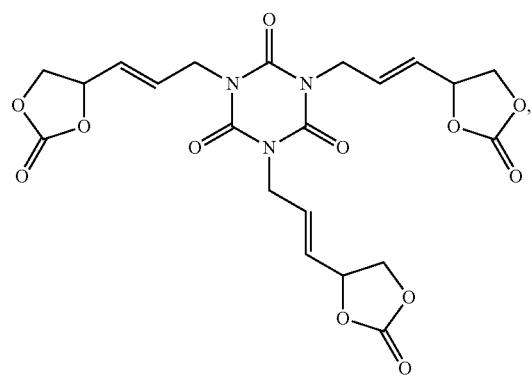

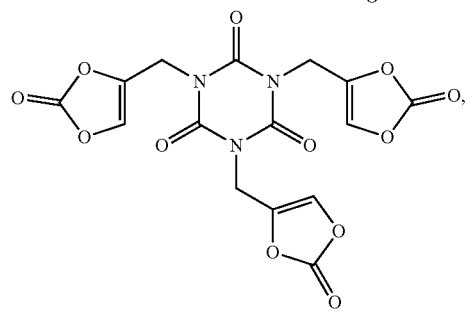

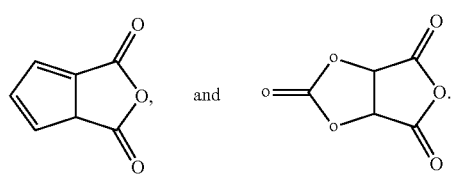

9. The electrolyte of claim 1 wherein at least one of the stabilizing additives is selected from the group consisting of:

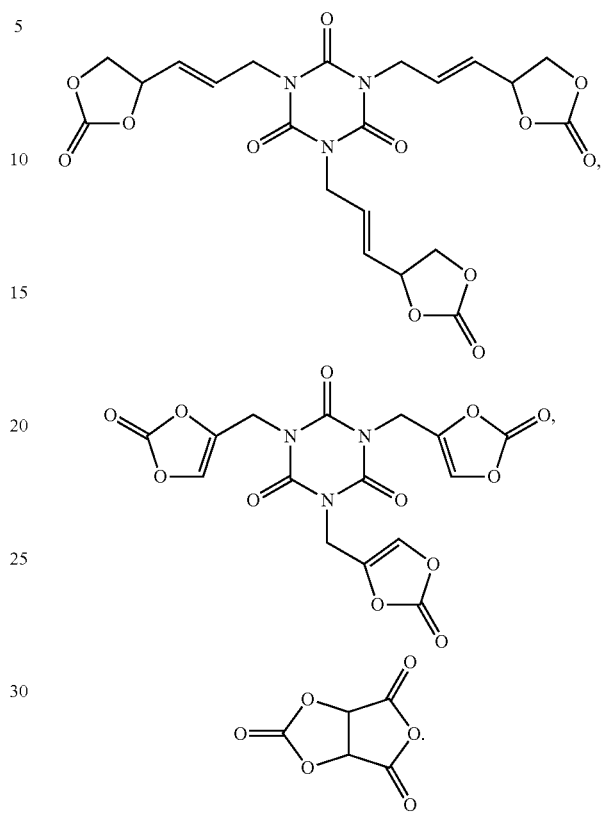

10. The electrolyte of claim 1 wherein at least one of the stabilizing additives is selected from the group consisting of:

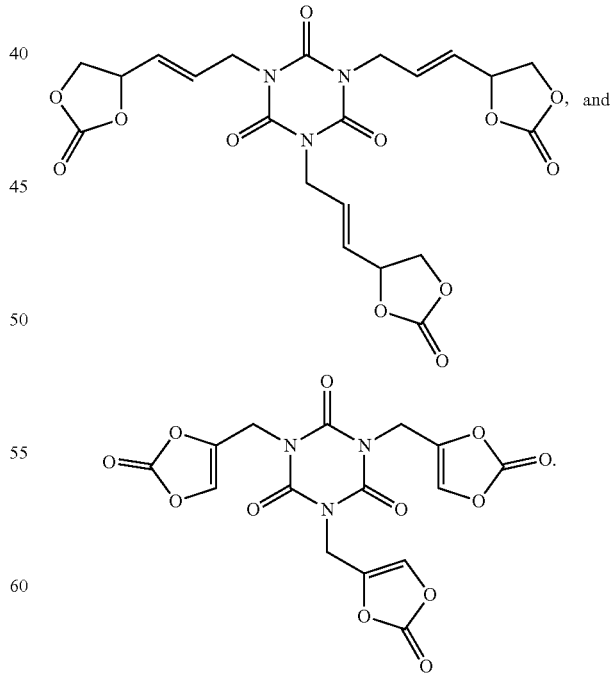

* * * * *